（12）United States Patent
Brown

(10) Patent No.: US 7,927,292 B2
(45) Date of Patent: Apr. 19, 2011

(54) SELF-POWERED VIBRATION SENSOR

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 62 days.

(21) Appl. No.: 11/683,472

(22) Filed: Mar. 8, 2007

(65) Prior Publication Data

US 2008/0221486 A1 Sep. 11, 2008

(51) Int. Cl.
*A61B 5/117* (2006.01)
*A61B 5/103* (2006.01)

(52) U.S. Cl. ........................................ 600/595

(58) Field of Classification Search .............. 600/300, 600/587, 595, 483, 484; 702/187, 189, 190; 320/132, 134, 136; 340/539.12, 573.1, 572.1; 324/432; 607/40; 128/920, 905, 921
See application file for complete search history.

(56) References Cited

U.S. PATENT DOCUMENTS

| 3,923,060 | A | 12/1975 | Ellinwood, Jr. | |
| 6,215,280 | B1* | 4/2001 | Cavazzini | 320/136 |
| 6,259,372 | B1 | 7/2001 | Taranowski et al. | |
| 6,478,736 | B1* | 11/2002 | Mault | 600/300 |
| 2001/0049470 | A1* | 12/2001 | Mault et al. | 600/300 |
| 2003/0163287 | A1* | 8/2003 | Vock et al. | 702/187 |
| 2005/0087019 | A1 | 4/2005 | Face | |
| 2005/0134452 | A1* | 6/2005 | Smith | 340/539.12 |
| 2005/0171452 | A1* | 8/2005 | Neff | 600/549 |
| 2007/0173705 | A1* | 7/2007 | Teller et al. | 600/300 |
| 2007/0255334 | A1* | 11/2007 | Keimel et al. | 607/40 |
| 2008/0162088 | A1* | 7/2008 | DeVaul et al. | 702/190 |

FOREIGN PATENT DOCUMENTS

| EP | 0 997 714 A2 | 5/2000 |
| WO | WO 2004/073138 A1 | 8/2004 |
| WO | WO 2006/046937 A1 | 5/2006 |
| WO | WO 2006/046989 A1 | 5/2006 |

OTHER PUBLICATIONS

Sodano et al, Generation and Storage of Electricity from Power Harvesting Devices, LA-UR-03-7148, JIMSS, 16(1), 67-75, 2005, pp. 1-18.*

* cited by examiner

*Primary Examiner* — Max Hlndenburg
*Assistant Examiner* — Brian Szmal
(74) *Attorney, Agent, or Firm* — Rahman LLC

(57) ABSTRACT

An apparatus, system, and method for monitoring vibration using a self-powered vibration sensor, a programmable interactive device, and a remote server. The self-powered sensor is capable of transforming vibrations into equivalent RF pulses, which are recorded and manipulated by the programmable interactive device. The programmable interactive device communicates the RF pulses to the remote server for further analysis, processing, and feedback. These interactions result in an objective monitoring of the vibration, which provides corrective feedback for beneficial transformation of behavior. The corrective feedback may be provided on a programmable interactive device such as a mobile phone, PDA, etc.

26 Claims, 3 Drawing Sheets

SELF-POWERED VIBRATION SENSOR

BACKGROUND

1. Technical Field

The embodiments herein relate generally to vibration monitoring and, more particularly, to a vibration monitoring and feedback system for behavior modification of a user.

2. Background

Vibration monitoring has long been used in industrial applications to monitor equipment for safety purposes. In such industrial applications, the equipment is understood to follow a standardized behavior pattern. The monitoring and security settings of the equipment are generally pre-defined and constant. Moreover, such applications do not typically require complex analysis of the effects of vibration on the equipment.

Recently, vibration monitoring has found a number of complex applications in the healthcare industry and other industries. In the healthcare industry, vibration monitoring and measurement may be used for obesity management, behavior analysis, and fitness training. The industry has recognized that vibration monitoring and measurement are very much appreciated for beneficial modification of biorhythmic activity and behavior.

In order to keep a record of activity, which may further provide an input for behavior modification, devices such as pedometers have been used. However, pedometers may have numerous mechanical and functional limitations. For example, in some applications, only certain movements such as walking may be counted using pedometers. Therefore, this does not provide a practical objective measurement of user activity.

Various advanced vibration monitoring devices may be used for better measurement of user activity. However, accelerometers and vibration monitoring devices commonly used in many applications may be expensive and complex. Further, in applications requiring numerous such devices the cost of application may become prohibitively high. Moreover, specialized power management systems may further make such implementations overly complex.

Therefore, there is a requirement of an accurate, yet cost-effective system for monitoring user activity. Further, a device that may function in conjunction with a monitoring and feedback system to closely monitor and help the user modify behavior patterns is required. Additionally, a personalized monitoring of user to provide a customized feedback is required.

SUMMARY

The embodiments herein provide a system, apparatus, and method for monitoring vibration for behavior modification of a user. In one embodiment, a self-powered sensor is capable of transforming vibrations into equivalent radio frequency (RF) pulses, which are recorded and manipulated by the programmable interactive device. The programmable interactive device communicates the RF pulses to the remote server for further analysis, processing, and feedback. These interactions result in objective monitoring of the vibration, which provides appropriate feedback for beneficial transformation of behavior.

The self-powered vibration sensor may be calibrated based on a comparison with reference data obtained from a known reference caloric measurement device such as a treadmill. In another embodiment, a plurality of self-powered vibration sensors may be integrated to form a network of sensor devices to communicate and interact simultaneously with the programmable interactive device.

Moreover, the embodiments herein provide an accurate and personalized vibration monitoring and customized feedback for improved behavior modification. The method thus provides a user with feedback on his behavior based on his latest user profile. The feedback may be made available to the user in the form of multimedia.

The self-powered aspect of the embodiments herein enables the implanting of the sensor in the user for long durations without requiring recharging of the battery or the removal and replacement of the sensor for battery maintenance. Additionally, the self-powered vibration sensor may be used to charge any other chargeable device. The feedback which may be provided in the form of reports updates the user on information on caloric burn, caloric intake, activity duration and the like.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF THE PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for an accurate, yet cost-effective system for monitoring user activity. Further, a device that may function in conjunction with a monitoring and feedback system to closely monitor and help the user modify behavior patterns is required. Additionally, a personalized monitoring of user to provide a customized feedback is required. The embodiments herein achieve this by providing a system, apparatus and method for monitoring vibration for behavior modification of user is described. In one embodiment, a self-powered sensor is capable of transforming vibrations into equivalent RF pulses, which are recorded and manipulated by the programmable interactive device based on a user profile that characterizes the user. The programmable interactive device communicates the RF pulses to the remote server for further analysis, processing, and feedback. These interactions result in the objective monitoring of the vibration, which provides appropriate feedback for the beneficial transformation of behavior. One aspect of the embodiments herein may be particularly applied as an device capable of being implanted in the user. Alternatively, the apparatus may be used as a device capable of being worn or carried by the user. In another embodiment, several sensors may be integrated to form a network of sensor devices to measure the vibration of different parts of the body simultaneously. These measurements may be used to develop a pattern of motion. The measurements and feedback provides a more detailed and richer information set about the activity being monitored.

Figure 1:
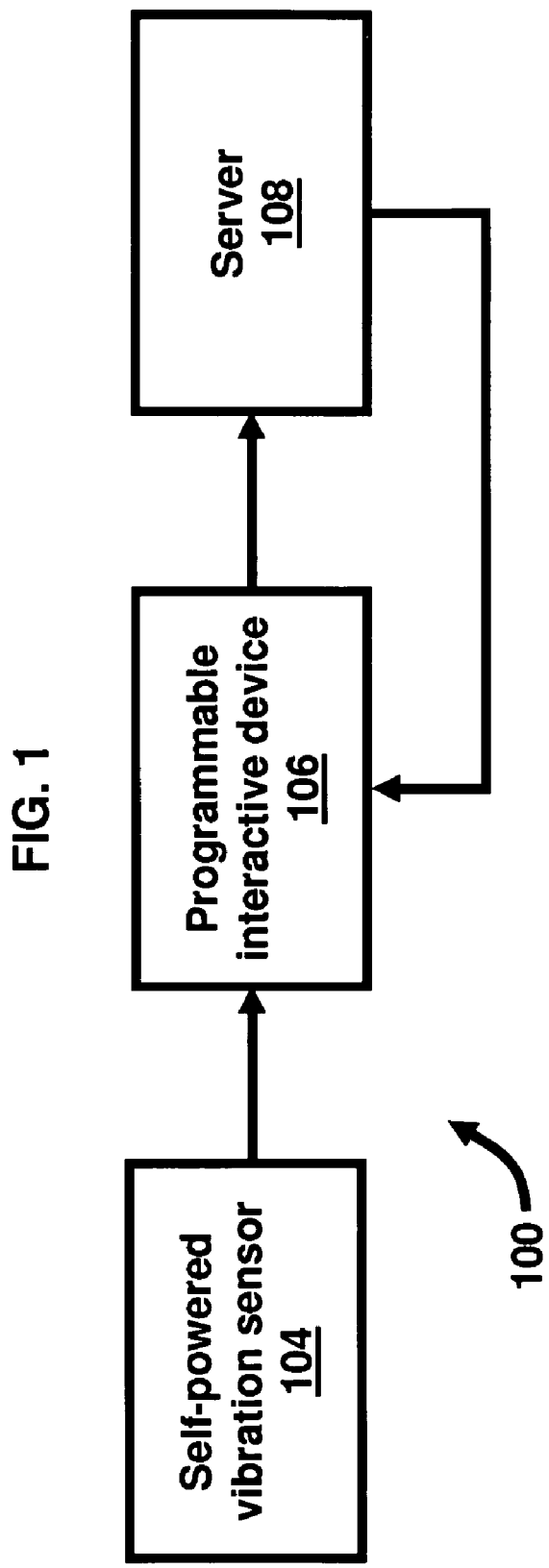
FIG. 1 is a block diagram illustrating an automatic vibration monitoring and feedback system according to an embodiment herein.
Figure 2:
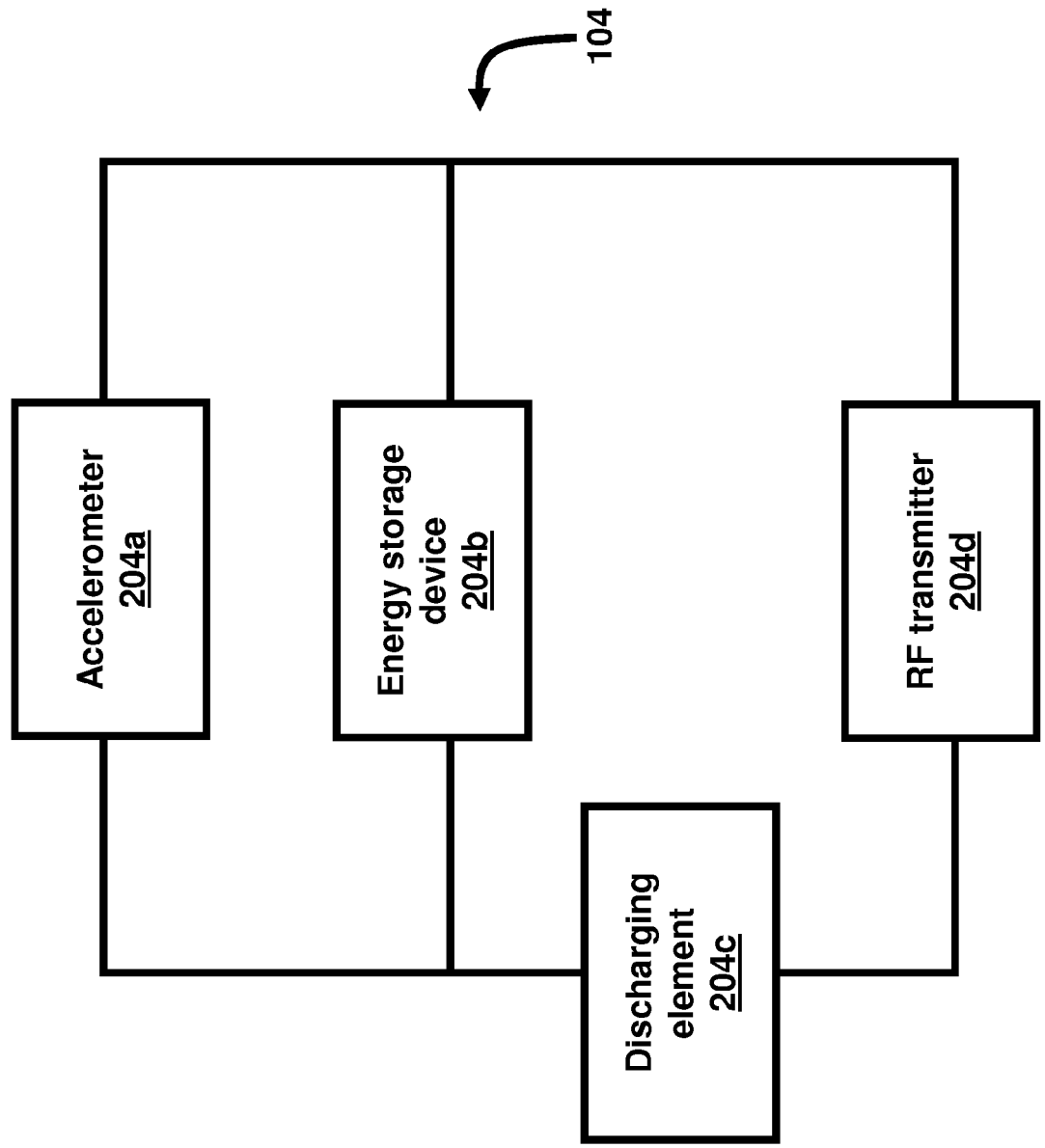
FIG. 2 is a block diagram of a self-powered vibration sensor according to an embodiment herein.
Figure 3:
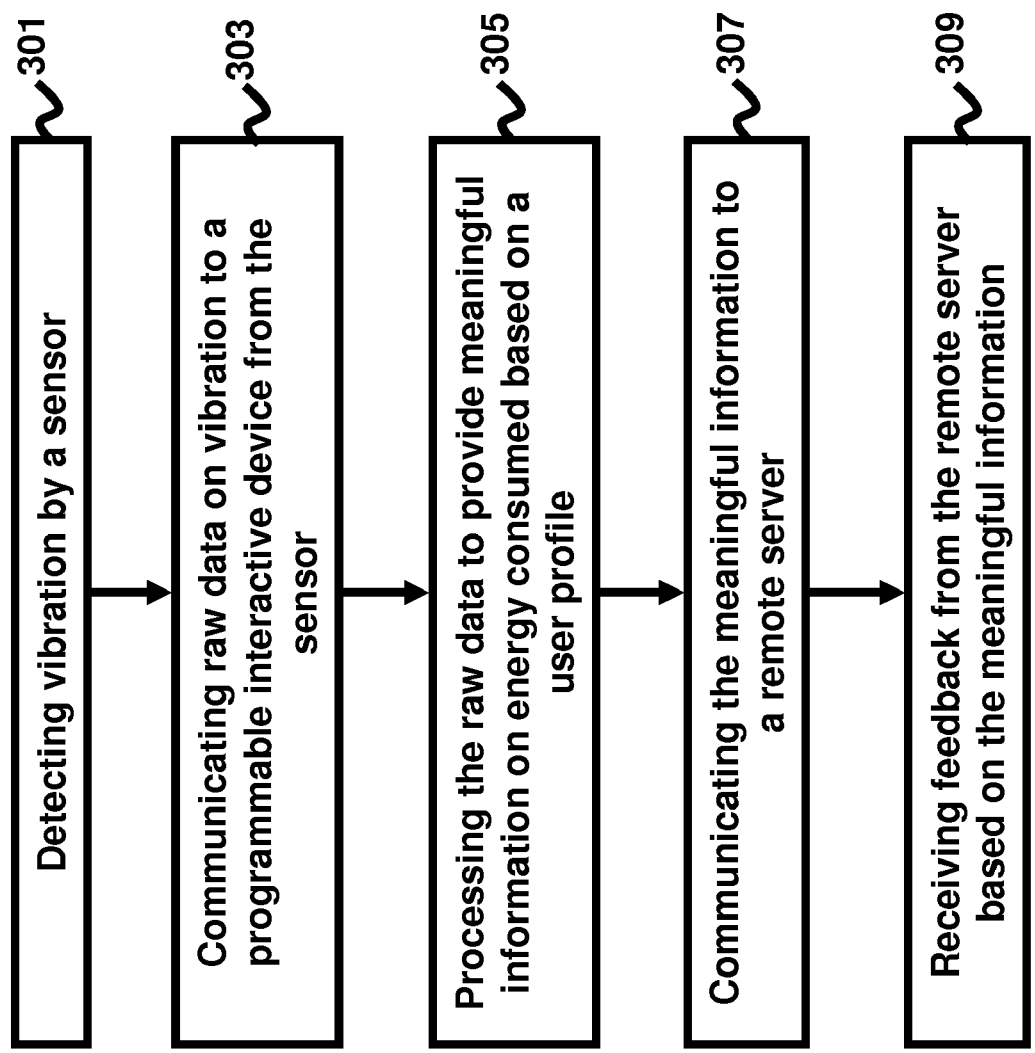
FIG. 3 is illustrates the method of automatic vibration monitoring and feedback according to an embodiment herein.

Referring now to the drawings, and more particularly to FIGS. 1 through 3, where similar reference characters denote corresponding features consistently throughout the figures, there are shown preferred embodiments. Reference in the specification to "one embodiment" or "an embodiment" means that a particular feature, structure, characteristic, or function described in connection with the embodiment is included in at least one aspect of the embodiments herein. Furthermore, the appearances of the phrase "in one embodiment" in various places in the specification are not necessarily all referring to the same embodiment.

FIG. 1 illustrates a general block diagram of an automatic vibration monitoring and feedback system 100 according to an embodiment herein. The system 100 includes a self-powered vibration sensor 104, which may sense various vibrations relating to the movement of a user (not shown). A programmable interactive device 106 is provided to communicate with the self-powered vibration sensor 104.

The self-powered vibration sensor 104 may be used to translate vibration into raw data in the form of RF pulses. The RF pulses may then be transferred to the programmable interactive device 106 that processes the RF pulses to form meaningful information. In this regard, "meaningful information" refers to information associated with the energy consumed by a user during some physical activity and is based on a user profile established by a user that may include information pertaining to the physical attributes of the user. Furthermore, the physical activity may include high-aerobic activities such as running, but it may also include more passive activities such as merely sitting or sleeping. The programmable interactive device 106 may be a mobile phone, a personal digital assistant (PDA), any other handheld computing network device, or any other network device.

In one embodiment, a plurality of self-powered vibration sensors 104 may be used in conjunction with one another to communicate with the programmable interactive device 106. In this regard, enhanced information on user activity and motion may be obtained by forming a network of such self-powered vibration sensors 104. Further, an objective measurement of the user movement enables better analysis of the motion.

In processing the raw data obtained by the sensor 104, the programmable interactive device 106 may utilize a user profile that characterizes the user. The programmable interactive device 106 may be calibrated based on these user interactive sessions. The interactive sessions are programmed to compare the RF pulses with reference data obtained from known reference caloric measurement devices such as a treadmill, etc. The user profile may be updated or modified based on the progress of the user and the other changes. The maintenance of a user profile enables the personalization of the meaningful information that is transmitted.

The meaningful information on a user may be transmitted to a server 108 for further analysis and feedback. The server 108 may include various applications required to analyze the meaningful information. The availability of detailed information from a plurality of such sensors 104 enables better feedback by the server 108 through the applications present. In another embodiment various applications may be linked with the server 108 through an internet network such as the World Wide Web in order to provide feedback based on the meaningful information obtained.

The system 100 thus allows for personalized information monitoring and customized feedback to the user. A plurality of users may be configured to be associated with a server 108. In another embodiment, the sensor 104, may be attached to a user's body, such as the waist area, or the sensor 104 may be implanted using different techniques such as sealing and housing in a smooth plastic vessel.

FIG. 2 further illustrates the self-powered vibration sensor 104 (of FIG. 1). The self-powered vibration sensor 104 is operable to convert vibrations into electric current, which may be used by various applications for further processing. The self-powered vibration sensor 104 may comprise an accelerometer 204a as a primary detecting element. The accelerometer 204a may detect the vibration of the user and transform the vibrations into equivalent electric current. Various types of accelerometers may be used in accordance with the embodiments herein. Preferably, a tri-axial accelerometer may be used to provide the measurement of vibrations. The tri-axial accelerometer based sensor 104 is sensitive to the acceleration, vibration, and motion along the three coordinate axes. Moreover, the performance or sensitivity of the sensor 104 remains consistence irrespective of the position where the sensor 104 is implanted in the user or worn by the user.

An energy storage device 204b may be provided to store the electric current produced by the accelerometer 204a. In one embodiment, the energy storage device 204b may be embodied as a capacitor. The energy storage device 204b may be provided to have a threshold value, wherein the energy storage device 204b, upon reaching the threshold value, starts discharging electric current to an RF transmitter 204d through a discharging element 204c. When a capacitor is used as the energy storage device 204b, the capacitance of the capacitor may be selectively chosen such that the discharge of the current occurs when the threshold value is reached. Further, the energy storage device 204b may be adapted to provide energy in the form of electrical current to any other chargeable device, which may require the energy in ranges of that produced by the accelerometer 204a. The sensor 104 may be so configured to provide equivalent information on vibration in such situations.

The timing of discharge may be controlled by the discharging element 204c. This provides the functionality of sampling and amplifying the electric current stored in the energy storage device 204b. Moreover, the discharging element 204c may be embodied as a gate or a timer, etc. In a gate embodiment, when the energy storage device 204b is fully charged, the gate releases the current to the RF transmitter 204d. In a timer embodiment, the timer determines intervals at which the current from the accelerometer 204a is sampled, amplified, and transmitted to the RF transmitter 204d.

Again, the electric current may be discharged to the RF transmitter 204d. The RF transmitter 204d is configured to translate electric current into RF pulses for further analysis, processing, and manipulation. The translation of electric current into RF pulses is such that the rate at which RF pulses that are produced is proportional to the electric current and thus proportional to the vibrations being measured. This allows for a simple cost effective implantable device that can be used for vibration monitoring without the need for a battery.

The cost of implementing many such devices in conjunction with one another to provide enhanced detailed information on user movement and activity may also be minimal. In such implementations, the frequency of transmission of RF pulses may be so decided to characterize the individual sensor 104. Furthermore, the RF transmitter 204d may be configured to transmit the RF pulses thereby providing raw data on the vibrations. The range of transmission required may vary and may be decided based on the application.

A method of automatic vibration monitoring and feedback according to the embodiments herein is illustrated in FIG. 3, with reference to FIGS. 1 and 2. The method provides for accurate and personalized vibration monitoring and customized feedback for improved behavior modification. The method may comprise detecting (301) vibration by a sensor 104 adapted to be associated with the user. The sensor 104 may be implantable. Alternatively, the sensor 104 may be wearable (i.e., worn) by the user.

The raw data obtained by the sensors 104 may be used for further processing by communicating (303) the raw data to a programmable interactive device 106. The programmable interactive device 106 for such purposes may be a mobile phone, a PDA, etc. The programmable interactive device 106 may be adapted to receive the raw data from the sensor 104. In another embodiment, the raw data from a plurality of sensors 104 may be communicated to the programmable interactive device 106.

Processing (305) of the raw data to provide meaningful information on energy consumed by the user as a result of physical activity and further based on a user profile may be undertaken at the programmable interactive device 106. Such a user profile may be built based on user interactive calibration sessions. This enables personalized information on user activity to be made available in the programmable interactive device 106. Further, such calibration sessions are configured to compare the meaningful information with reference data obtained from a known reference caloric measurement device. This ensures correctness and verification of user interactive calibration sessions. Additionally, the method also allows for modified user profile maintenance based on the improvements and changes taking place in the user. Such a user profile, thus, characterizes the user with the periodic updates to include the latest changes.

Analysis of the meaningful information may occur by communicating (307) the meaningful information to a server 108, which may be located in a remote location. The server 108 may be configured to analyze and process the meaningful information obtained from the programmable interactive device 106. Moreover, customized feedback to the user may be provided by the applications attached to the server 108. The personalized information of the users obtained enables the server 108 to provide accurate information to the applications for better feedback.

The user may be updated on his/her progress by receiving (309) feedback from the remote server 108 based on the meaningful information at the programmable interactive device 106. Thus, the method provides a user with the feedback on his behavior based on his latest user profile. The feedback may be made available to the user in the form of multimedia. Accordingly, an interface (not shown) for such purposes may be provided in the programmable interactive device 106. Also, the feedback may be made available in the form of text that a user may read and adhere to.

The embodiments herein provide a system 100 for better vibration and activity monitoring. The sensor 104 provided by the embodiments herein is sensitive to the acceleration, vibration, and motion along the three coordinate axes instead of one or two axes. Moreover, the performance or sensitivity of the sensor 104 remains consistent irrespective of the wearable or implantable position of the sensor 104 in/on the user's body. The self-powered aspect of the sensor 104 enables the implantation of the sensor 104 in the user's body for long durations without requiring recharging of a battery or removal and replacement of the sensor 104 for battery maintenance. Additionally, the self-powered vibration sensor 104 may be used to charge any other chargeable device.

The embodiments herein provide the user with accurate, virtually instantaneous and continuing feedback on their current level of activity through a feedback technique. Use of the feedback output in the embodiments herein has been found to offer a clear indication of current activity levels and maintenance of a desired level of activity performance. In addition, an alternate embodiment provides a longer time period of data accumulation for a more cumulative indication of a user's prolonged activity level.

The adjustable features of the embodiments herein further provide continual flexibility and "feedback training". The "training" takes into account user activity improvements and increases in the user's endurance. In yet another embodiment, the feedback may alternatively reflect a sensed level of activity increase, or acceleration, by changing the character of the feedback with increases in activity levels.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An automatic vibration monitoring and feedback system comprising:
  a self-powered vibration sensor that detects vibrations of a user, produces a plurality of radio frequency (RF) pulses at a rate that is directly proportional to the detected vibration, and transmits said RF pulses, wherein said self-powered vibration sensor comprises a non-battery component comprising an accelerometer that detects vibration and converts the detected vibration into equivalent electric current, wherein said vibration comprises of acceleration and motion across three coordinate axes;
  a programmable interactive device in wireless communication with said self-powered vibration sensor, wherein said programmable interactive device receives said RF pulses from said vibration sensor and converts said RF pulses into meaningful information, wherein said meaningful information is associated with energy consumed by said user based on a user profile that is periodically modified; and
  a server that is remotely linked to said programmable interactive device, wherein said server comprises computer applications that receive said meaningful information from said programmable interactive device and provide feedback to said programmable interactive device based on said meaningful information, wherein said programmable interactive device is calibrated to build said user profile based on user interactive calibration sessions, and wherein said calibration sessions are programmed in said programmable interactive device to compare said RF pulses with reference data obtained from a known reference caloric measurement device.

2. The automatic vibration monitoring and feedback system of claim 1, wherein said sensor is adapted to be worn by said user.

3. The automatic vibration monitoring and feedback system of claim 1, wherein said sensor is adapted to be implanted in said user.

4. The automatic vibration monitoring and feedback system of claim 1, wherein said server analyzes and processes said meaningful information.

5. The automatic vibration monitoring and feedback system of claim 1, wherein said feedback is in the form of text.

6. The automatic vibration monitoring and feedback system of claim 1, wherein said programmable interactive device interacts simultaneously with a plurality of said sensors.

7. The automatic vibration monitoring and feedback system of claim 1, wherein a plurality of said sensors are integrated to form a network of sensor devices.

8. The automatic vibration monitoring and feedback system of claim 1, wherein said accelerometer comprises a tri-axial accelerometer.

9. The automatic vibration monitoring and feedback system of claim 1, further comprising:
an energy storage device operatively connected to said accelerometer, wherein said energy storage device stores said electric current;
a RF transmitter operatively connected to said energy storage device and said accelerometer; and
a discharging element operatively connected to said energy storage device, said accelerometer, and said RF transmitter, wherein said discharging element comprises any of a gate and a timer.

10. The automatic vibration monitoring and feedback system of claim 9, wherein said energy storage device comprises a threshold value, wherein said energy storage device, upon reaching said threshold value, starts discharging electric current to said RF transmitter through said discharging element.

11. The automatic vibration monitoring and feedback system of claim 9, wherein said energy storage device comprises a capacitor, and wherein said timer determines an interval to sample, amplify and transmit said stored electric current to said RF transmitter.

12. A self-powered vibration sensor comprising:
a non-battery electromechanical component comprising an accelerometer that detects vibration and converts the detected vibration into electric current;
an energy storage device operatively connected to said accelerometer, wherein said energy storage device stores said electric current;
a discharging element directly connected to said energy storage device, wherein said discharging element determines a time period for discharging said electric current, and wherein said discharging element comprises any of a gate and a timer; and
a radio frequency (RF) transmitter operatively connected to said discharging element, wherein said RF transmitter converts said electric current into RF pulses at a rate directly proportional to said electric current, wherein said sensor recharges a chargeable device operatively connected to said sensor.

13. The self-powered vibration sensor of claim 12, wherein said energy storage device comprises a capacitor.

14. The self-powered vibration sensor of claim 12, wherein said sensor is implanted in a user.

15. The self-powered vibration sensor of claim 12, wherein said sensor is adapted to be worn by a user.

16. The self-powered vibration sensor of claim 12, wherein said accelerometer comprises a tri-axial accelerometer.

17. The self-powered vibration sensor of claim 12, wherein said energy storage device comprises a threshold value, wherein said energy storage device, upon reaching said threshold value, starts discharging electric current to said RF transmitter through said discharging element.

18. A method for automatic vibration monitoring and feedback, said method comprising:
detecting vibration of a user by a sensor that comprises a non-battery component comprising an accelerometer that detects vibration and converts the detected vibration into equivalent electric current, wherein said vibration comprises of acceleration and motion across three coordinate axes;
wirelessly communicating, from said sensor, raw data directly proportional to the detected vibration to a programmable interactive device;
processing said raw data to provide meaningful information, wherein said meaningful information is associated with energy consumed by a user based on a user profile that is periodically modified;
communicating said meaningful information to a server comprising computer applications, wherein said server is remotely linked to said programmable interactive device; and
receiving, in said programmable interactive device, feedback in the form of multimedia from said server based on said meaningful information,
wherein said programmable interactive device is calibrated to build said user profile based on user interactive calibration sessions, and
wherein said calibration sessions periodically update said user profile and are programmed in said programmable interactive device to compare said raw data with reference data obtained from a known reference caloric measurement device.

19. The method of claim 18, wherein said raw data comprises radio frequency (RF) pulses that are produced at a rate proportional to said detected vibration.

20. The method of claim 19, wherein said programmable interactive device counts a number of RF pulses.

21. The method of claim 18, wherein said server analyzes and processes said meaningful information.

22. The method of claim 18, wherein said server provides feedback and reports to said programmable interactive device.

23. The method of claim 22, wherein the report provides information on any of caloric burn, caloric intake, and activity duration of said user.

24. The method of claim 18, wherein said accelerometer comprises a tri-axial accelerometer.

25. The method of claim 18, further comprising:
operatively connecting an energy storage device to said accelerometer, wherein said energy storage device stores said electric current;
operatively connecting a RF transmitter to said energy storage device and said accelerometer; and operatively connecting a discharging element to said energy storage device, said accelerometer, and said RF transmitter, wherein said discharging element comprises any of a gate and a timer.

26. The method of claim 25, wherein said energy storage device comprises a threshold value, wherein said energy storage device, upon reaching said threshold value, starts discharging electric current to said RF transmitter through said discharging element.

* * * * *